United States Patent [19]
Miller

[11] Patent Number: 5,940,166
[45] Date of Patent: Aug. 17, 1999

[54] BINOCULAR INDIRECT OPHTHALMOSCOPE

[76] Inventor: Joel A. Miller, 2940 Orchard Pl., Orchard Lake, Mich. 48324

[21] Appl. No.: 08/928,949

[22] Filed: Sep. 12, 1997

[51] Int. Cl.⁶ ..................................................... A61B 3/10
[52] U.S. Cl. ............................................ 351/221; 351/205
[58] Field of Search ..................................... 351/221, 205, 351/214, 200, 246; 128/645, 395, 398

[56] References Cited

U.S. PATENT DOCUMENTS

| | | | |
|---|---|---|---|
| 3,592,525 | 7/1971 | Schultz | 350/146 |
| 4,061,423 | 12/1977 | Pomerantzeff | 351/16 |
| 4,166,677 | 9/1979 | Heine et al. | 351/16 |
| 4,684,227 | 8/1987 | Schmidt et al. | 351/205 |
| 5,252,999 | 10/1993 | Sukigara et al. | 351/221 |
| 5,268,711 | 12/1993 | Poxleitner et al. | 351/214 |
| 5,333,018 | 7/1994 | Heine et al. | 351/221 |

*Primary Examiner*—Hung Xuan Dang
*Attorney, Agent, or Firm*—Gifford, Krass, Groh, Sprinkle, Anderson & Citkowski, P.C.

[57] ABSTRACT

A binocular indirect ophthalmoscope is disclosed having a housing with a pair of eyepieces. The housing itself is removably secured to the head of the user, typically an ophthalmologist. An optical system is contained within the housing for reflecting light along a viewing axis through each of the eyepieces. An illumination system is also provided for directing an illuminating light beam along an illumination axis. This illumination system includes a source of light remote from the housing and an optical fiber which optically couples the light source to the housing. The remote location of the light source reduces the weight of the ophthalmoscope and eliminates dangerous overheating of the headpiece.

6 Claims, 1 Drawing Sheet

BINOCULAR INDIRECT OPHTHALMOSCOPE

BACKGROUND OF THE INVENTION

I. Field of the Invention

The present invention relates generally to medical devices and, more particularly, to a binocular indirect ophthalmoscope.

II. Description of the Prior Art

Binocular indirect ophthalmoscopes, hereafter called ophthalmoscopes, are used by ophthalmologists for examining the eye and particularly the retina of the eye. The previously known ophthalmoscopes include a housing having two eyepieces, one for each eye. The housing is then removably secured to the head of the user by a head strap so that one eyepiece is aligned with each eye of the user.

An optical system, typically comprising a pair of mirrors and a prism, is also contained within the ophthalmoscope. This allows for directing reflected light from the patient's eye outwardly through the housing and then through each eyepiece. This constitutes the viewing axis for the ophthalmoscope.

In order to provide sufficient illumination through the pupil of the eye so that the retina can be seen, these previously known ophthalmoscopes include a tungsten or halogen light bulb contained within the housing between and above the eyepieces. The light from the light bulb is then reflected by a mirror or other optical means along a variable illumination axis and thus parallel to the viewing axis of the ophthalmoscope.

These previously known ophthalmoscopes, however, suffer from a number of disadvantages. One disadvantage is that the light bulb becomes quite hot after prolonged use which correspondingly heats the housing of the ophthalmoscope. In doing so, the ophthalmoscope becomes uncomfortably warm for the user. The light source must have a heat sink which adds weight to the ophthalmoscope. This added weight can cause fatigue or stress in the viewer's cervical spine.

A still further disadvantage of the illuminating means for these previously known ophthalmoscopes is that the light bulbs are relatively fragile. As such, the filaments within the light bulbs are prone to breakage from even small impacts to the ophthalmoscope housing.

Lastly, the ophthalmoscope must be removed from the examiner's head when the examiner wishes to begin operating on the patient's eye. During the course of an operation the ophthalmoscope is often placed back on the examiner's head and removed again. The frequent removal and replacement of the instrument is necessary because separate loupes are required for magnification of the eye during surgery.

SUMMARY OF THE PRESENT INVENTION

The present invention provides a binocular indirect ophthalmoscope which overcomes all of the above-mentioned disadvantages of the previously known devices.

In brief, like the previously known devices, the ophthalmoscope of the present invention comprises a housing having a pair of eyepieces. The housing itself is removably attached to the head of the user so that, in doing so, one eyepiece registers with each eye.

An optical system, typically comprising a pair of mirrors and a prism, is contained within the housing so that light from the viewing axis, is directed to each eyepiece. Consequently, in use, the optical image provided to each eyepiece is aligned with the illumination axis.

Unlike the previously known ophthalmoscopes, the present invention provides a light source remote from the ophthalmoscope housing. This light source can comprise a laser, halogen bulb, xenon bulb or the like. By remotely locating the light source the weight of the ophthalmoscope can be reduced. The instrument does not become hot with long periods of use.

An optical fiber or other equivalent means is then utilized to optically couple the light from the light source to the ophthalmoscope housing. In doing so, the light output from the optical fiber directs the light into the ophthalmoscope housing and preferably about a vertical axis from the top of the housing. A mirror, prism or other optical means is then employed to reflect the light from the optical fiber along the illumination axis.

Additionally, the present invention preferably includes a pair of magnifying loupes (or telescopes) which are secured to the ophthalmoscope housing so that one magnifying loupe is provided below each eyepiece. The magnifying loupes allow a magnified view of the external eye from a comfortable working distance without requiring the time consuming removal of the ophthalmoscope and use of separate telescopic loupes.

BRIEF DESCRIPTION OF THE DRAWINGS

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
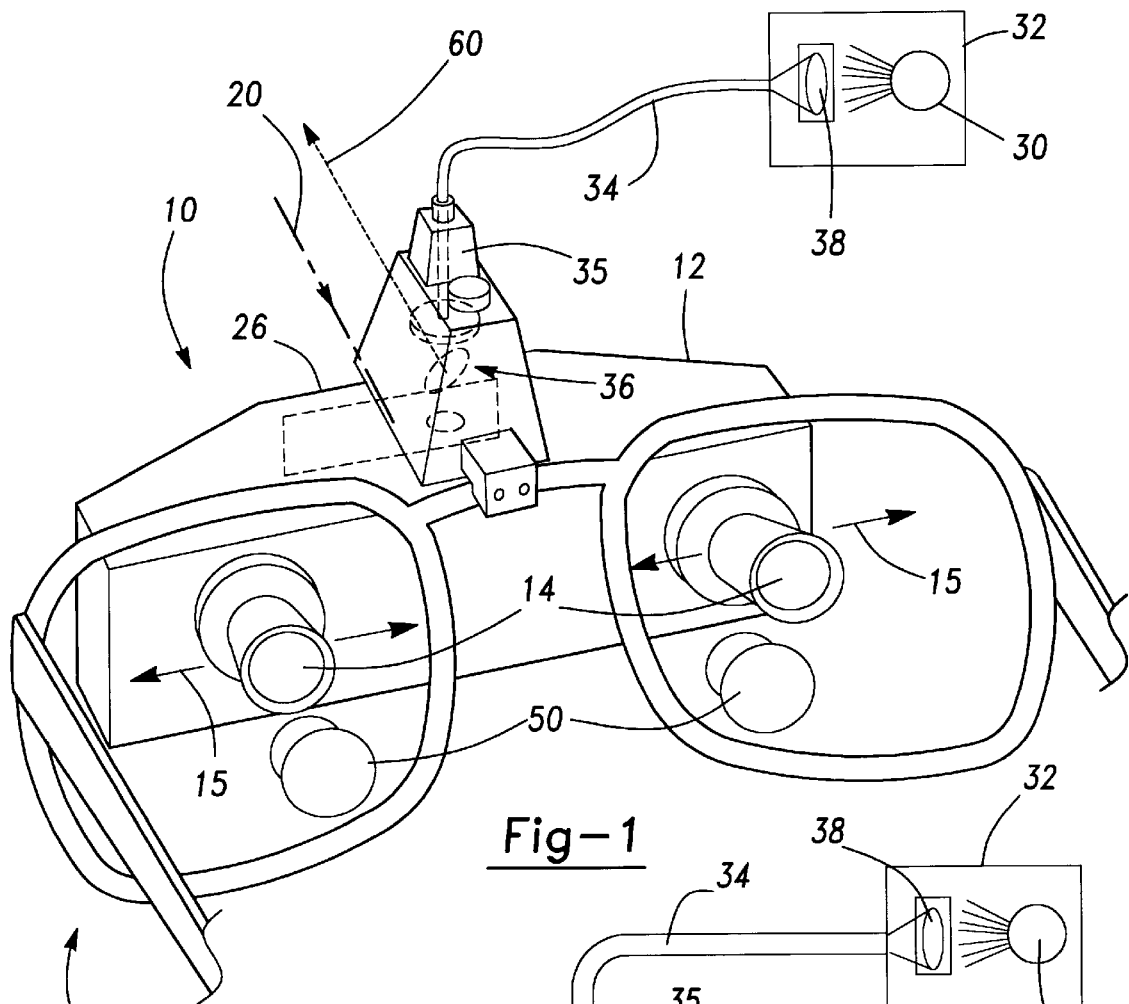
FIG. 1 is an elevational rear view illustrating a preferred embodiment of the present invention.

With reference first to FIG. 1, a preferred embodiment of the binocular indirect ophthalmoscope 10 of the present invention is there shown and comprises a housing 12 having two eyepieces 14. The housing 12 is adapted to be detachably secured to the head of a user by an eyeglass frame 16 (only partially shown) so hat, in doing so, one eyepiece 14 registers with each eye of the user. The lateral spacing between the eyepieces 14 is adjustable as indicated by arrows 15 to accommodate different users in any conventional fashion.

Figure 2:
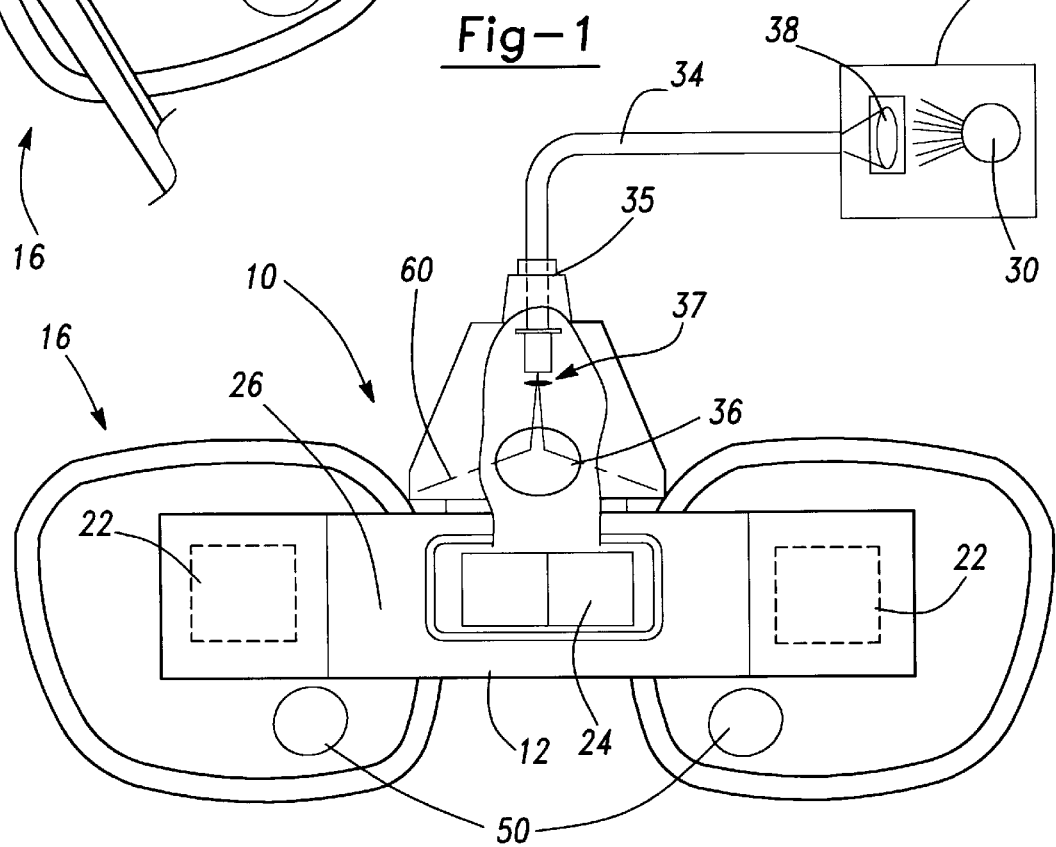
FIG. 2 is a front plan view illustrating the preferred embodiment of the present invention.

With reference now to FIGS. 1 and 2, an optical system is contained within the interior of the housing 12 for reflecting light along a viewing axis 20 (FIG. 1) to each of the eyepieces. The optical system includes a mirror 22 (FIG. 2) associated with each eyepiece 14 as well as a prism 24 disposed between the mirrors 22. The viewing axis 20 extends generally perpendicularly outwardly from a front side 26 of the ophthalmoscope housing 12. Preferably, the viewing axis 20 is aligned with the center of the housing 12.

In order to provide illumination along the illumination axis 60, a light source 30 is contained within a housing 32 in a position remote from the ophthalmoscope housing 12. The light source 30 may comprise any light source such as a laser or a halogen, tungsten, or a xenon bulb or the like.

In order to optically couple the light source 30 to the illumination axis 60, an elongated optical fiber 34 extends from the light source housing 32 to the ophthalmoscope housing 12 and preferably to the top 35 of the ophthalmoscope housing 12 along its center line. In doing so, the light output from the optical fiber 34 is directed generally vertically downwardly into a mirror 36 within the ophthalmoscope housing 12. The mirror can be tilted to vary the illumination axis 60. Conventional means, such as a lens 38, are also preferably contained within the interior of the light source housing 32 to focus the light from the light source 30 into the optical fiber 34. A lens 37 (FIG. 2) is also optionally employed within the housing 12 to focus the light along the axis 20.

With reference now particularly to FIG. 1, the mirror 36 is used to align the illumination axis 60 with the viewing axis 20. The output axis 60 is parallel and close to the viewing axis 20.

The light source 30 together with its housing 32 can be positioned at any convenient place. The housing 32 can even be secured, for example, to the waist or belt of the user. However, unlike the previously known ophthalmoscopes, since the light source 30 is remote from the housing 12, the previously known disadvantages of having the light source contained within the ophthalmoscope housing 12 are completely avoided.

Referring now to FIGS. 1 and 2, a still further improvement of the present invention is that a telescopic loupe 50 is attached piggyback to below the eyepiece 14, or directly to the eyeglass frame 16 adjacent each eyepiece 14. These loupes allow the user, typically an ophthalmologist, to examine the exterior eye under magnification without removing the ophthalmoscope. The examiner may have his or her spectacle correction placed within the lens frame 16.

From the foregoing, it can be seen that the present invention provides a novel binocular indirect ophthalmoscope which overcomes the disadvantages of the previously known devices. Having described my invention, however, many modifications thereto will become apparent to those skilled in the art to which it pertains without deviation from the spirit of the invention as defined by the scope of the appended claims.

I claim:

1. A binocular indirect ophthalmoscope comprising:

a housing having a pair of eyepieces, means for removably securing said housing to a head of a user, an optical system contained in said housing for reflecting light along a viewing axis to each of said eyepieces, an illumination system for directing an illuminating light beam along an illumination axis, said illumination system comprising a source of light remote from said housing, means for optically coupling said light source to said housing, and means in said housing for directing said light source along said illumination axis, and a pair of telescopic loupes secured to said housing so that one loupe is adjacent each eyepiece, said loupes being optically isolated from said optical system.

2. The invention as defined in claim 1 wherein said optical coupling means comprises an optical fiber.

3. The invention as defined in claim 1 wherein said light source comprises a laser.

4. The invention as defined in claim 1 wherein said light source comprises a halogen light source.

5. The invention as defined in claim 1 wherein said directing means comprises a mirror aligned with said illumination axis.

6. The invention as defined in claim 1 wherein said directing means comprises a pair of mirrors, one mirror aligned with each eyepiece, and a prism contained in said housing between said mirrors.

* * * * *